United States Patent [19]

Wilson

[11] 4,213,207
[45] Jul. 22, 1980

[54] ARTIFICIAL HEART AND METHOD OF PUMPING BLOOD

[76] Inventor: Frederick M. Wilson, 2308 Lakeside Dr., Arlington, Tex. 76013

[21] Appl. No.: 894,546

[22] Filed: Apr. 7, 1978

[51] Int. Cl.² .......................... A61F 1/24; A61M 1/03
[52] U.S. Cl. ........................................ 3/1.7; 128/1 D; 417/418
[58] Field of Search ............ 3/1.7; 128/1 D, DIG. 3; 417/415–418

[56] References Cited

U.S. PATENT DOCUMENTS

| | | | |
|---|---|---|---|
| 3,134,938 | 5/1964 | Morgan | 417/418 X |
| 3,791,769 | 2/1974 | Kovacs | 3/1.7 X |
| 3,791,770 | 2/1974 | Farkos | 417/418 |
| 3,842,440 | 10/1974 | Karlson | 3/1.7 |
| 3,884,125 | 5/1975 | Massie | 417/418 X |

FOREIGN PATENT DOCUMENTS 2309206 11/1976 France ........................ 3/1.7

*Primary Examiner*—Ronald L. Frinks
*Attorney, Agent, or Firm*—Charles W. McHugh

[57] ABSTRACT

A construction having utility as a replacement for one or both chambers of a human heart, constituting a pump which operates in accordance with solenoid principles. A hollow and firm cylindrical member of non-magnetic material has an inlet port and an outlet port at each end. A check valve is associated with each of the ports, so that blood may be both admitted and expelled from each end of the cylinder. A ball which is responsive to a magnetic field rolls or floats within the cylinder. A magnetic field, typically obtained from passing current through an electrical coil, is alternately established at one end of the cylinder and then the other end, whereby the ball will oscillate to and fro—pushing blood ahead of it. Clearance between the ball and the inside wall of the cylinder insures at least some reverse flow of blood, cleaning the ball with each stroke. Electrical circuitry is provided to adjust at least one of the electrical pulse parameters, including frequency, amplitude and duty cycle. With reed-actuated switches, the pump actuation can be varied at will or "fine tuned" after it has been implanted in a chest cavity.

16 Claims, 6 Drawing Figures

ARTIFICIAL HEART AND METHOD OF PUMPING BLOOD

This invention relates generally to pumps, and more particularly it relates to a pump which may be used in association with a human body as a replacement for or supplement to a natural heart. Specifically, it relates to a solenoid-type apparatus in which the movable core is a ball.

There have been many attempts from time to time to design a mechanical pump which is as efficient as the human heart for pumping blood. One reason that these numerous attempts have met with less success than might be desired is the unique characteristics of human blood. Indeed, it may be fairly said that whole blood is a rather difficult liquid to pump outside of the human body. In particular, great care must be exercised to avoid any harsh mechanical working or agitation which could cause structural damage to either the platelets or cells in the blood. If too many red cells are inadvertently ruptured, thereby releasing their hemoglobin into the bloodstream, rather severe consequences may result. Also, blood is known to be a rather corrosive liquid, and relatively few materials are completely immune to its corrosive affects. Even some plastics that were once thought to be excellent candidates for use in a blood-pumping system have been found to be inadequate for long term use. For example, some polyethylene resins reportedly lose one-third of their tensile strength after only 18 months in the body.

In addition to considerations relating to blood, there are other factors that must be considered in designing a pump if the pump is to be implanted within a person's chest cavity in order to replace or supplement the natural action of that person's heart. For example, the overall size and shape of the pump must be suitable for implantation in the chest cavity. Also, there must be some efficient manner of delivering power to the pump in order to render it operative. Additionally, an artificial heart should not only be characterized by great durability and reliability, but also it would be desirable to have a pump which could be adjusted to fit the unique requirements of a particular person in which the pump is to be implanted. Furthermore, it would be desirable to have an implanted pump which is capable of being controlled from outside the body, such that pump operation may be adjusted after the pump has been implanted. All of these things are believed to be goals that heretofore have eluded designers. Indeed, insofar as is known, there has not been a single example of a mechanical heart that has been successfully implanted in a human body and left there to perform the function of a natural heart over an extended period of time. Accordingly, it is a primary object of this invention to provide a reliable pump which is serviceable as a replacement for a human heart.

It is another object to provide an artificial heart which has a self-cleaning characteristic that inherently avoids any region of stagnant blood.

Still another object is to provide an implantable heart which utilizes two or more solenoids for moving a magnetic ball from one end of a tubular chamber toward the other end.

A further object is to provide a pump which inherently draws in a fresh supply of blood during each stroke of expelling the previously accumulated quantity of blood.

These and other objects will be apparent from a reading of the specification and the claims appended thereto, as well as an examination of the attached drawings in which:

In brief, the invention includes first and second rigid and cylindrical chambers for replacing the atrium and ventricle functions in a human heart. Each non-magnetic chamber has two ports at each end, with one of the two ports being adapted to serve as an inlet port and the other being adapted to serve as an outlet port. Conventional check valves are associated with each of the ports. A pair of independent electrical coils are associated with each of the two cylindrical chambers, with one coil being at a chamber's first end and the other coil being at the opposite end. A metallic member, typically a free-floating ball, is contained within each chamber where it may be alternately attracted by the magnetic fields resulting from current flowing alternately through the electrical coils. Electrical circuitry is provided for adjusting the frequency, amplitude and duty cycle of pulses supplied to the respective coils, such that the artificial heart may be "fine tuned" to the unique requirements of a particular individual.

Figure 1:
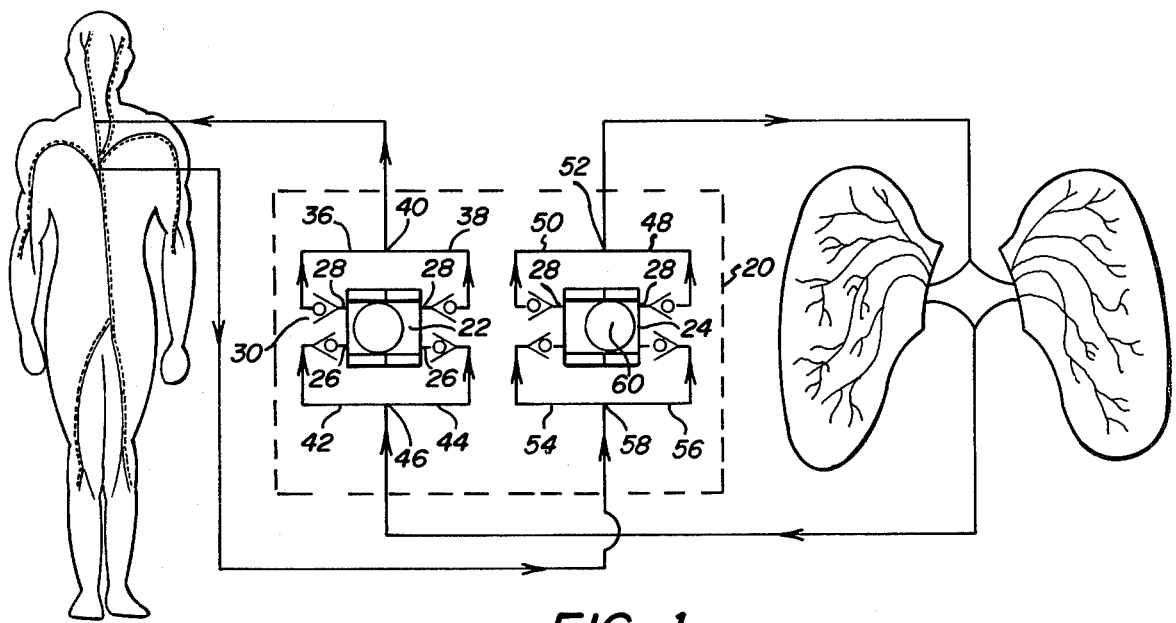
FIG. 1 is a schematic showing of a solenoid-type pump in accordance with the invention which is specifically adapted to serve as an artificial heart.

Referring initially to FIG. 1 the prosthetic heart 20 of the invention includes first and second rigid and cylindrical chambers 22, 24 for replacing the atrium and ventricle functions in a human heart. The cylindrical chambers are made of a non-magnetic material that can be sterilized and which is compatible with human blood. Furthermore, in those embodiments where the prosthetic heart is to be implanted within a chest cavity, the material of the chambers must also be compatible with the human body so as to minimize the risk of adverse body reactions. A suitable material is polyester velour. The diameters of the two chambers 22, 24 may be identical, although a difference in the two might be advantageous—in view of the fact that the left ventricle has a slightly greater work load in pumping oxygen-rich blood through the aorta to the body. The length of each cylindrical member 22, 24 will be at least one inch, and somewhat more than two inches would be more common for a prosthetic heart for an adult. The ends of the hollow cylinders 22, 24 are closed, but they each have two spaced inlet ports 26 and two spaced outlet ports 28. One of each type of port (inlet and outlet) is placed at each end of a respective chamber 22, 24. Associated with each of the ports 26, 28 is a check valve 30, so that the direction of flow into and out of a respective chamber will be controlled in a desired manner. A suitable check valve is disclosed in U.S. Pat. No. 3,911,502 to Boretos.

Surrounding each of the cylindrical chambers 22, 24 in this embodiment are a pair of side-by-side coils 32, 34. Preferably, the coils 32, 34 are more nearly tall than they are flat, such that the coils extend longitudinally along a respective cylinder for a greater distance than they extend radially outward from said cylinder. An exemplary electrical coil might have about 2000 turns of No. 24 wire; the ID of the coils would be about 2¼ inches, which is just enough to fit over the outer wall of a respective cylinder 22, 24. The OD of a coil 32, 34 would typically be about 2¾ inches, and the height (or length) of the coil would typically be about one inch.

The two outlet ports 28 of one of the cylindrical chambers 22 are respectfully connected to two passages 36, 38, which in turn are joined through a Y-fitting 40 which connects through its central leg to the aorta circuit of a human body. The two inlet ports 26 of cylindrical chamber 22 are respectively connected to passages 42, 44 which in turn are connected through Y-fitting 46 to the pulmonary vein leading from the human's lungs. Hence, the cylindrical chamber 22 is adapted to pump blood from the lungs into the body circuit.

With regard to the other cylindrical chamber 24, its two outlet ports 28 are connected through passages 48, 50 which are, in turn, connected through Y-fitting 52 to the pulmonary artery, whereby the output of chamber 24 supplies blood under pressure to the lungs. The inlet ports 26 of chamber 24 are connected through passages 54, 56 to a Y-shaped fitting 58 which, in turn, is connected through its central leg to the superior vena cava, whereby chamber 24 draws its blood from the body circuit.

Contained within each of the two cylinders 22, 24 is a metallic member 60 which is made of material having properties such that it will be attracted by the magnetic field resulting from current flowing through the electrical coils 32, 34 which surround each of the cylinders 22, 24. The metallic member 60 is preferably a free-rolling ball made of an inert material such as one of the magnetic stainless steels. For light weight, the ball 60 is preferably hollow; but it should have a specific gravity approximating that of blood. The outside diameter of a ball 60 is sufficiently less than the inside diameter of its associated cylinder so as to foster at least some reverse flow of blood as the ball is alternatively attracted to first one and then the other of the two coils 32, 34. The reason for providing this reverse flow of a small quantity of blood is to promote cleaning of the ball as well as clearing and cooling of the cylinder and the ball. This reverse flow can be established by providing a clearance of about 0.030 inch between the interior wall of the cylinder and the outer diameter of a ball 60.

While the magnetic field alone may be enough to keep a ball 60 suspended and centered within a coil 32, 34, it is advantageous to mechanically insure appropriate placement of a ball 60 with regard to the cylinders 22, 24—by providing a set of longitudinal members in the form of three or more rails 52 that extend longitudinally along the inside wall of the chambers 22, 24 for the full excursion length of the balls 60. The amount of blood pumped by a single pumping cycle will therefore be established by multiplying the cross-sectional area of a ball times its excursion length in moving from one coil to the other, minus such blood as escapes rearwardly around the ball 60 during a given excursion.

One reason for favoring a ball (such as magnetic ball 60) over a different structural shape, such as a cylinder, is that a ball will roll in response to sequentially applied magnetic fields. A rolling or floating ball is not as prone to cause structural damage to any blood platelets or cells as would a structure characterized by sliding motion. Too, a floating ball will not tend to establish a fixed wear pattern, and it almost inevitably exposes different parts of its surface to the blood moving through a chamber 22, 24, so that the desired cleaning action on the ball is obtained. (If the moving member was a cylinder rather than a ball, it might be possible to create a quantity of blood that remains nearly static between the cylindrical surfaces of a chamber 22 and the moving element; eventually this might lead to the formation of a clot that would have obvious adverse consequences.)

Figure 2:
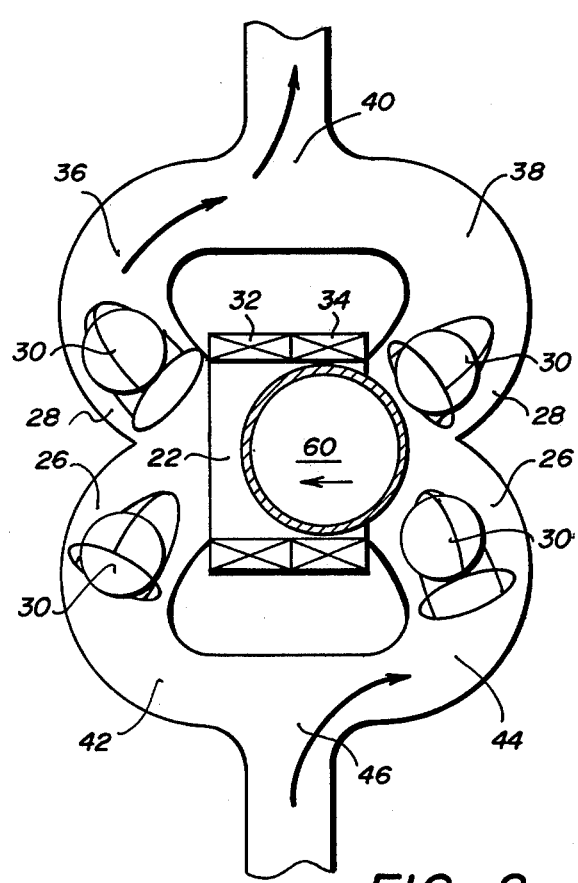
FIG. 2 is a diagrammatic showing of one chamber of an artificial heart, showing the flow path of blood through the chamber when the ball moves from right to left in response to a magnetic attractive force at the left end of the cylindrical chamber.
Figure 3:
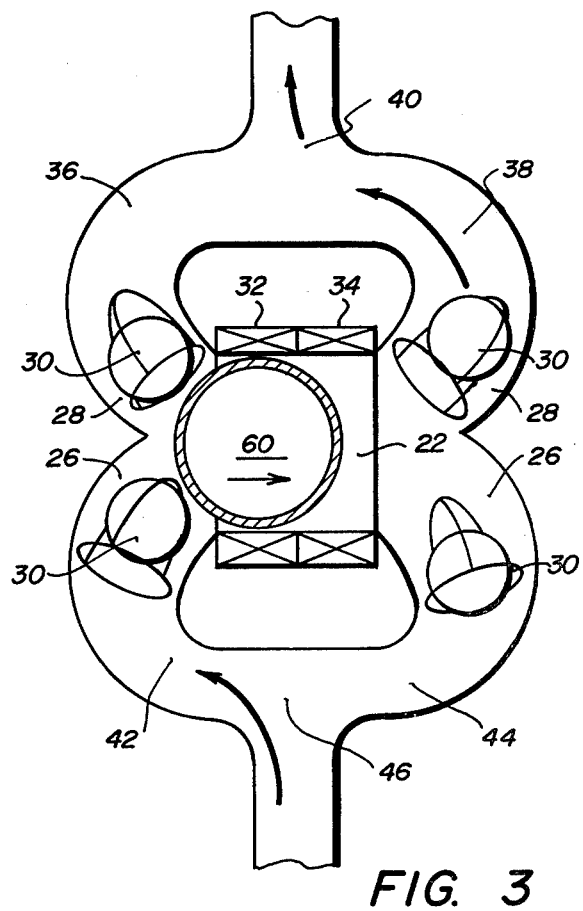
FIG. 3 is a view similar to FIG. 2 in which the flow of blood through the chamber is reversed by virtue of a magnetic field being established at the right side of the cylindrical chamber.

Another advantage of the double-ended chambers 22, 24 disclosed herein is there is no portion of the artificial heart 20 that is not subjected to a complete cleansing flow with full cycle of ball movement. That is, there are no secluded corners or pockets in which stagnant blood might accumulate. Since each end of a respective chamber has both in-coming and out-going blood, there is essentially no chance for any quantity of blood to be static for long. This advantage of the invention may perhaps be better appreciated from a comparison of FIGS. 2 and 3, in which the ball 60 of one chamber is shown at opposite ends of its excursion path. Still another advantage of this particular prosthetic heart—in comparison with some other designs—is that a failure of the electrical power will not create a mechanical obstacle to the flow of blood through a person. That is, if the power to coils 32, 34 should be lost and the ball 60 became static, blood could still pass through the pairs of check valves at each end of the cylinder—if some external pump was available to pressurize the blood and push it through the body.

Figure 5:
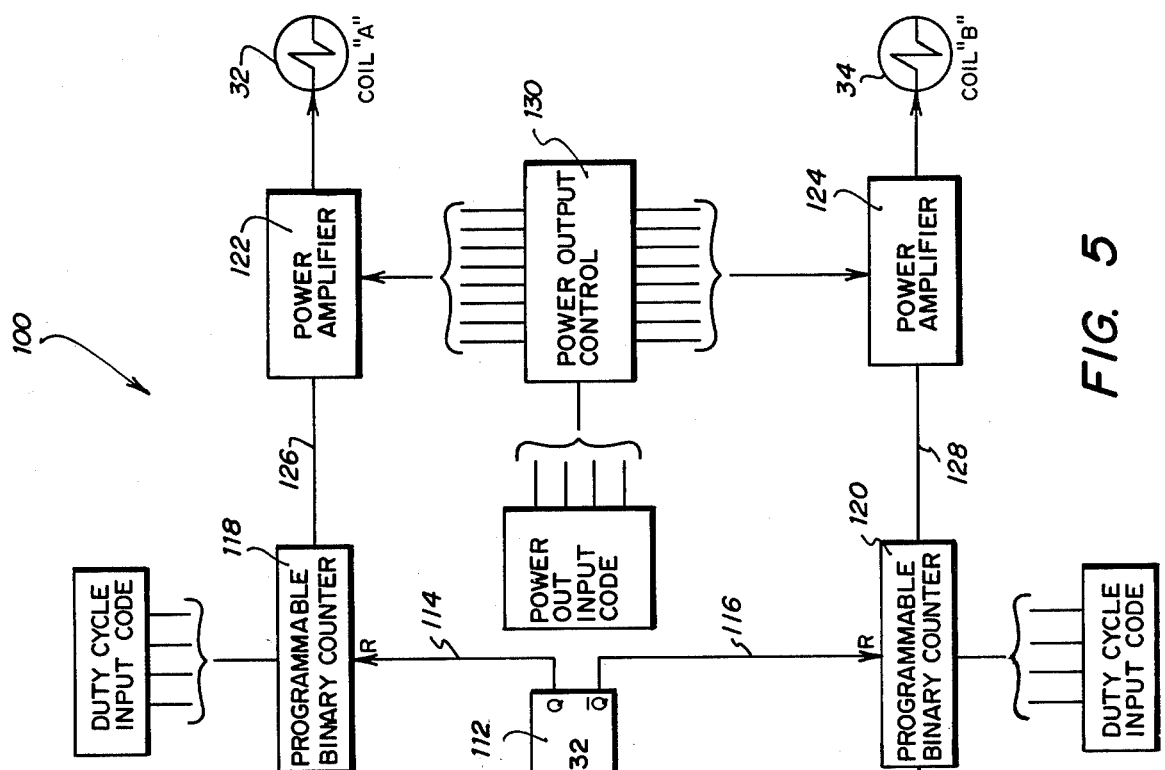
FIG. 5 is a block diagram of an electrical circuit which is suitable for powering the coils shown in a chamber such as that shown in FIG. 2.
Figure 6:
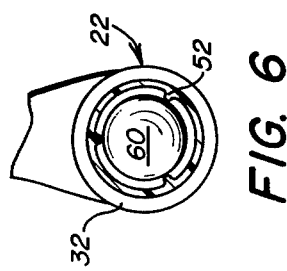
FIG. 6 is a transverse sectional view through a cylindrical chamber showing the ball held away from the interior wall by a set of structural rail members.
Figure 4:
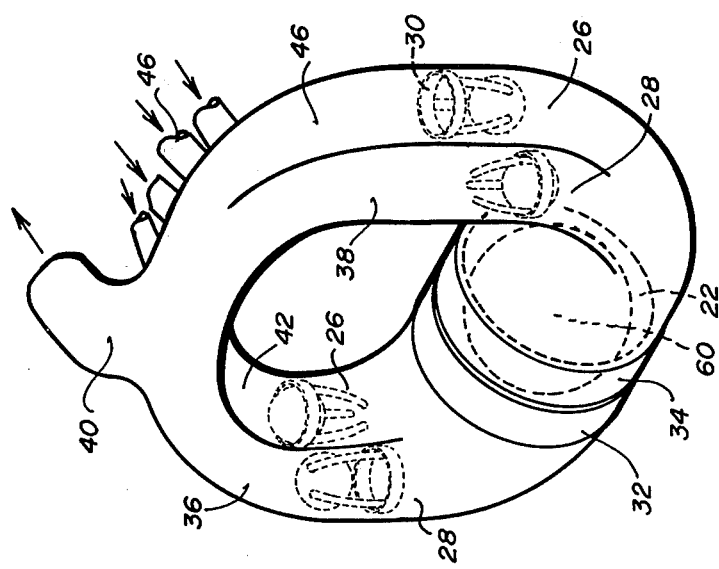
FIG. 4 is a perspective view of one chamber which has a configuration approximating that which would be suitable for implantation in the chest cavity of a person.

Referring next to FIG. 5, the electrical circuitry for alternately energizing first one and then the other of a pair of coils is shown. Of course, this circuit is not intended to be limiting—in view of the fact that circuitry for alternately energizing two loads can be largely a matter of choice to the designer. The one basic parameter that will likely be respected in any event is that approximately 10 watts of power may be required by the heart if it performs the task of pumping about 60 ml of blood at a pressure of about 180 mm Hg. Of course, the work load on the prosthetic heart will naturally vary in accordance with the activity of the person at any given time, with about 1½ watts reportedly being required for a sleeping person, 4 watts being required for a person performing light chores, about 7 watts being required for a person climbing stairs and perhaps 12 watts being needed for more strenuous work.

The technique for furnishing the required power to a prosthetic heart may also be a matter of some choice. There have been proposals, for example, to implant a nuclear-powered steam engine within a person's chest cavity as a means of providing the power to operate an artificial heart. Another alternative is to provide a transcutaneous power transformer, with the primary coil being suspended externally of the wearer and being connected to some continuous, rechargeable or replaceable power source. Permanently buried just below the skin would be the secondary coil of the transformer, and this coil would be connected to the electrical controls and the coils 32, 34 adjacent a given cylinder. The advantage of utilizing a transcutaneous transformer (with one coil being inside the body and the other coil being outside the body) is that it avoids the risk of infection that might arise from any wires or tubes that passed through a person's skin. Of course, if the problem of infection from a wire passing through the skin could somehow be solved, then such a solution would facilitate the transfer of power to a prosthetic heart within a person's body.

In view of the critical nature of a prosthetic heart in keeping a person alive, it would naturally be desirable to have some sort of a backup system available to immediately receive power from a non-biological source and convert that power into a pumping action. In the embodiment of FIG. 1, this backup capability may be at least partially realized by providing four coils rather than two for each of the cylindrical chambers 22, 24. The first pair of coils, designated for convenience as the primary coils, would be adapted to move the magnetic ball 60 to and fro at the required frequency; it is known that a natural heart beats about 60–90 times per minute, and there should therefore be about 60–90 excursions of the ball, i.e., about 30–45 full cycles of ball movement. If an electrical failure should occur in one of the primary coils, the solid state controls mounted on the artificial heart would sense the interruption of current through the primary coils and automatically switch the flow of current to the alternate coils. In this way, the most sensitive part of the system—and the part most likely to fail if there is to be a failure—would have a backup system. An embodiment having multiple coils would operate in all other respects like the previously disclosed embodiment.

In addition to use of the apparatus described herein as a prosthetic heart adapted for being installed within a person's chest cavity, it is quite feasible that the apparatus would serve as a pump to be maintained outside of the body in the same way that the transfusion pumps are presently employed. An example of such a pump is shown in U.S. Pat. No. 2,925,814 to Vibber and St. Jean. Also, a part of the apparatus disclosed herein could be utilized as a "heart assisted" apparatus, being mounted essentially in parallel with the left ventricle portion of a biologic heart. During those times when it is desirable to lend assistance to a person's natural heart, the unit could be energized at the right time to furnish such assistance. On the other hand, when the person may be sleeping and his requirement for pumping of blood is appreciably reduced, it might be possible to lower the power input to the respective coils, furnishing only enough power to keep blood circulating through the cylindrical chamber so that it does not have a chance to clot, etc.

Referring next to FIG. 5, an electrical circuit 100 is shown which will provide control for a ball pump in such a way that the pump will approximately duplicate the function of a human heart. The primary power source is not shown in this drawing, and the power source is not intended to constitute a portion of this invention. Instead, the extensive work by others in the field of transcutaneous transformers, wherein implanted batteries which are recharged by mutual induction through a person's skin, will typically be relied on to obtain power for the circuit.

The circuit 100 shown in FIG. 5 serves only one of an artificial heart's two chambers, and the second chamber will typically be controlled by an essentially identical circuit. Under certain circumstances, however, if the strengths of the electrical signal to coils A and B are great enough, said signals might also serve the second chamber; this would be possible because the two chambers of an artificial heart always operate simultaneously, and they do a comparable amount of work—in terms of moving blood.

The circuit 100 includes three variable controls which may be programmed (typically by a doctor) from outside the body in order to affect movement of the ball in the solenoid-type pump. Hence, with the circuit disclosed herein, an artificial heart can be implanted within a person's chest cavity and subsequently adjusted or "fine tuned" to fit the person's unique physical needs. One of the variable controls is adapted to adjust the pulse rate—preferably from about 50 to 93 beats per minute, which is the range that a doctor would likely wish to have in a prosthetic heart. Additionally, the speed of ball movement may be adjusted by varying the magnetic field realized from coils A, B. This particular control feature will be referred to herein as the duty cycle control, and will be described in more detail hereinafter.

The other variable control is actually a power control, and may be thought of as an adjustment of the strength with which the ball moves from one position to another—in pumping blood ahead of it. In other words, the power control may be said to determine how much work the blood pump will do in terms of displacing blood by forcing it through the person's arteries, veins, and capillaries.

Electrical coils A and B of a typical chamber 22, 24 are alternately energized with an electrical signal which is controlled as to its frequency, amplitude and duty cycle. To achieve a heart pulse rate of about 50 to 90 beats per minute, a clock or oscillator 108 provides a signal of about 200 hertz, which serves as the input to a divide-by-N device 110. The value of N is established by a binary input code which may be adjusted by opening or closing certain reed switches in the pulse rate control. Typical values for N may be within the range of 8 to 15.

Clock generator 108 may be any one of many known devices for generating a train of clock pulses at a constant, uniform rate. The output of divider 110 is applied to a flip flop 112 having complementary Q and Q̄ outputs which appear on lines 114 and 116, respectively. Flip-flop 112 may be a decade counter/divider such as MC14017B available from Motorola; it is utilized in the circuit 100 as a divide-by-32 device, such that the output from clock generator 108 is sequentially divided by devices 110 and 112. The output of divider 110 is also applied to programmable counters 118, 120 which are respectively associated with the two coils A, B of a given chamber.

The programmable counters 118, 120 may be divide-by-N, 4-bit counters such as MC14526B binary counters manufactured by Motorola. In this circuit, the counters 118, 120 are employed to establish the duty cycle of the apparatus, which—in effect—establishes the portion of each pulse which is applied to a respective coil. By use herein of the expression duty cycle, it is meant to refer to the ratio of two times, i.e., the pulse ON time divided by the pulse width. The duty cycle in this circuit may be adjusted from 56.25 percent to 100 percent by selecting a desired one of eight binary inputs to the counters 118, 120. By applying a binary input code from "0" to "7", a counter 118, 120 will turn on and stay on until it receives a "reset" signal from the flip flop 112 through connector 114 or 116. A signal from flip flop 112 will return a counter 118, 120 to zero.

The output signal from counters 118, 120 are respectively applied to amplifiers 122, 124 through connectors 126, 128. Also, connected to amplifier 122 through appropriate circuitry is power output device 130, which may be a 4-bit latch/4-to-16 line decoder such as MC14515B decoder available from Motorola. The latches for such a device 130 are R-S type flip-flops which hold the last input data presented prior to the strobe transition from "1" to "0". Four input terminals are used for the four-digit binary inputs, and the fifth terminal is used to "seal in" the selected binary input. The output of power device 130 is from a single one of 16 output lines, each providing a different value ranging from, say, 3 to 12 volts, with the different voltages being obtained by virtue of resistors of different values which are connected to respective ones of the 16 output terminals.

Each of the above-mentioned devices having variable encoders, magnetically actuated reed-control switches are included. If these switches are physically located just below a person's skin, they may be altered at will after the prosthetic heart has been implanted within a person's chest cavity. That is, the input codes to the devices 110, 118, 120, 130 can be established with transcutaneous encoders. In this way, a doctor may alter either the frequency, amplitude or duty cycle of the apparatus shown herein at any desired time; and, the apparatus can be "fine tuned" to a person's physical needs—even if those needs change from month to month or year to year. Those skilled in the art will recognize, of course, that suitable labeling of the switch locations (as by tatooing the skin, etc.) will be appropriate for proper identification of certain switches from outside the body. Furthermore, it should be understood that other switching devices could be substituted for the reed switches disclosed herein; and any equivalent technique for controlling the electrical circuit should be deemed to fall within the broad concept of the invention.

Those skilled in the art will no doubt also appreciate that the selection of particular materials for the components described herein will naturally be chosen in accordance with their compatibility with human blood, etc. With regard to any metallic components, those materials which are known to be attacked by blood will typically be insulated with a covering of Teflon or the like. With regard to the firm cylinders 22, 24 in which the movable member 60 oscillates, any strong material (perhaps even rubber-like in its properties) should be satisfactory, provided that it does not deteriorate with age as a result of prolonged exposure to body fluids. To the extent that somewhat resilient materials for the chambers are found to be unreliable, the more trustworthy rigid materials (such as filled Teflons or polypropylene, etc.) may be required.

While the movable member 60 has been referred to herein as metallic, it should be understood that it could also be made of a molded plastic in which metallic particles are embedded, so that the member will respond to a magnetic field. However, it is believed that a metallic ball will tend to provide better response characteristics than would a metal-filled plastic ball. And, it is also believed that a metallic ball will meet the requirements of buoyancy and light weight better than would most plastics. In choosing a material for a metallic ball 60, it will perhaps be advantageous for the designer of a movable member 60 to think in terms of a metallic ping pong ball, i.e., a ball having relatively thin walls and a low mass.

While only the preferred forms of the invention have been described herein, together with certain logical extensions thereof, it should be apparent to those skilled in the art that further modifications could be accomplished without departing from the spirit of the invention. Hence, variations of the structures disclosed herein should be understood to fall within the scope of the invention—which should be limited only by the claims appended hereto. For example, the specific configuration of a cylinder and the location of the various valves, etc., may be largely a matter of choice—depending upon the space available in a person's chest cavity and the condition of other organs, etc. Too, while the volume of blood moved through the "left" and "right" artificial chambers must be the same, it would be entirely within the scope of the invention to obtain a higher pressure in one chamber than the other—by putting more turns of wire in, for example, the left coil. Fortunately, the inherent leakage around a moving ball will tend to prevent the creation of sufficient vacuum so as to risk collapse of a vein or lower the vapor pressure to the degree that an individual blood cell might rupture. To this extent, then, the invention disclosed herein offers a self-regulating characteristic that is not available with previously known devices; and great versatility in both design and operation of an artificial heart is made possible with the disclosed features.

What is claimed is:

1. A construction having utility as a replacement for one chamber of a human heart, comprising:
    (a) a hollow and firm cylindrical member of non-magnetic material having a length of more than one inch, with the two ends of the cylindrical member being closed, and there being an inlet port and an outlet port at each end of the cylindrical member;
    (b) a check valve mounted in association with each of the ports, with one of the check valves at each end being oriented so as to admit blood to the cylindrical member in response to a low pressure therein, and the other check valve at a given end of the cylindrical member being oriented to discharge blood from the cylindrical member in response to a high pressure therein;
    (c) a movable member sized to translate within the cylindrical member and being configured as a ball that is slightly smaller in diameter than the inner diameter of the cylindrical member, whereby translating the ball at a substantial speed will cause blood ahead of the ball to be pushed forwardly; and
    (d) means for causing the movable member to translate within the cylindrical member at a desired time.

2. The construction as claimed in claim 1 wherein the means for causing the movable member to translate includes a pair of electrical coils adjacent the cylindrical member, with one of the electrical coils being positioned near a first end of said cylindrical member and the second coil being positioned near the opposite end of said cylindrical member, whereby the passing of electrical current alternately through the two coils will cause a magnetic field to be established at alternate ends of the cylindrical member.

3. Apparatus adapted for use in a prosthetic heart, comprising:

(a) a firm and cylindrical chamber formed of nonmagnetic material, and the chamber being adapted for replacing the atrium and ventricle functions of a portion of a human heart, with said chamber having an inlet port and an outlet port at each end;

(b) a check valve in each of said inlet and outlet ports in said chamber; and (c) a ball movable within the cylindrical chamber for causing blood to be pumped through respective ones of the inlet and outlet ports; and (d) a set of structural members mounted within the cylindrical chamber and being adapted for holding a ball away from the interior wall of the chamber as the ball rolls within said chamber.

4. The apparatus as claimed in claim 3 wherein the set of members for holding a ball away from the chamber's interior wall constitutes a set of at least three longitudinal rails affixed to the side of the chamber's wall, and the rails being substantially equally spaced around the chamber's interior.

5. Apparatus adapted for use in a prosthetic heart, comprising:

(a) a rigid and cylindrical chamber adapted for replacing the atrium and ventricle functions of a portion of a human heart, and said chamber having an inlet port and an outlet port at each end, and there being a check valve in each of said inlet and outlet ports, and there also being electric coils adjacent each end of the cylinder for creating a magnetic field when current flows therethrough;

(b) a free-floating ball contained within the cylinder, with said ball having characteristics such that it is attracted by the magnetic field resulting from current flowing through the electrical coils, and the outside diameter of a ball being significantly less than the inside diameter of the cylinder so as to foster at least some reverse flow of blood around the ball in order to promote cleaning and clearing of the cylinder and the ball; and (c) electrical means for passing current alternately through the electric coils so as to cause the ball to oscillate between the two ends of the chamber.

6. The apparatus as claimed in claim 5 and further including means for adjusting at least one of the parameters of the pulsed current which is passed through the electric coils, with said parameters including frequency, amplitude and duty cycle.

7. The apparatus as claimed in claim 6 wherein at least one parameter of the pulsed current which passes through the electric coils is adjustable after the apparatus has been implanted within a person's chest cavity.

8. The apparatus as claimed in claim 5 wherein the electric coils are positioned circumferentially around the cylindrical chamber.

9. The apparatus as claimed in claim 5 and further including a first common tube connected to each of the inlet check valves, and a second common tube connected to each of the outlet check valves, and there being a fitting for providing communication between a respective tube and the blood circulation system of a person, whereby blood may be supplied from a person's body to both ends of the chamber and also expelled from both ends of the chamber back into the blood circulation system.

10. A prosthetic heart adapted to accomplish the functions of a natural heart, comprising:

(a) first and second rigid and cylindrical chambers for replacing the atrium and ventricle functions in a human heart, and each of said chambers having two spaced inlet ports and two spaced outlet ports, with one of each type of port being on each end of a respective chamber, and there being a check valve in each of said inlet and outlet ports, and there also being a pair of side-by-side coils surrounding each cylinder, with each coil being configured to create a wide magnetic field when current flows therethrough, with one of the chambers being adapted to pump blood to the body circuit and the other chamber being adapted to pump blood to the lung circuit, and each chamber being adapted to receive blood from the opposite circuit through its respective inlet ports;

(b) a free-floating ball contained within each of the two cylinders, with each ball having physical properties such that it is attracted by the magnetic field resulting from current flowing through the electrical coils surrounding the cylinders, and the outside diameter of a ball being sufficiently less than the inside diameter of its associated cylinder so as to foster some reverse flow of blood in order to promote cleaning and clearing of the cylinder and the ball;

(c) electrical circuitry for alternately energizing first one and then the other of a pair of coils on each chamber, such that a ball will be alternately attracted toward one end and then the other end of a given cylinder, whereby blood ahead of a moving ball will be displaced; and (d) means for energizing said electrical circuitry.

11. The prosthetic heart as claimed in claim 10 and further including a set of structural members in each cylinder for holding a ball away from the interior wall of the cylinder as a ball moves within said cylinder.

12. The method of pumping blood, comprising the step of:

moving a ball through a cylindrical tube containing blood, with the outer diameter of the ball being slightly less than the inner diameter of the cylindrical tube, and the speed of movement of the ball being sufficient to push at least most of the blood ahead of the ball instead of allowing any great quantity of blood to escape around the ball.

13. The method of pumping blood as claimed in claim 12 wherein the cylindrical tube has an inlet and an outlet at each end of the tube, and the blood is pumped by causing the ball to reciprocate within the cylindrical tube.

14. The method of pumping blood as claimed in claim 12 wherein the ball includes at least some magnetically attractable material, and the ball is caused to move within the cylindrical tube by virtue of selectively establishing a controlled magnetic field adjacent the cylindrical tube.

15. The method of pumping blood as claimed in claim 14 wherein the cylindrical tube is non-magnetic, and there are at least two electrical coils adjacent the tube, with one of the two coils being at each end of the tube, and the ball is caused to reciprocate within the tube by alternately energizing first one and then the other of the electrical coils.

16. The method of pumping blood as claimed in claim 12 wherein the clearance between the outer diameter of the ball and the inner diameter of the cylindrical tube is on the order of 0.030 inch, such that moving the ball within the cylindrical tube causes at least some blood to escape around the ball in a direction opposite to the direction of ball movement, and whereby the escaping blood has a velocity that promotes clearing and cleaning of the cylindrical tube and the ball.

* * * * *